(12) United States Patent
Fugo et al.

(10) Patent No.: US 6,867,387 B2
(45) Date of Patent: Mar. 15, 2005

(54) DEVICE FOR PLASMA INCISION OF MATTER WITH A SPECIFICALLY TUNED RADIOFREQUENCY ELECTROMAGNETIC FIELD GENERATOR

(76) Inventors: Richard J. Fugo, 1507 Plymouth Blvd., Plymouth Meeting, PA (US) 19462; Damian Coccio, 2139 Yarnall Rd., Pottstown, PA (US) 19464

( * ) Notice: Subject to any disclaimer, the term of this patent is extended or adjusted under 35 U.S.C. 154(b) by 0 days.

(21) Appl. No.: 10/457,998

(22) Filed: Jun. 10, 2003

(65) Prior Publication Data
US 2003/0213780 A1 Nov. 20, 2003

Related U.S. Application Data

(63) Continuation of application No. 09/999,477, filed on Oct. 31, 2001, which is a continuation-in-part of application No. 09/112,471, filed on Jul. 9, 1998, now Pat. No. 6,479,785.

(51) Int. Cl.[7] ............................................. B23K 10/00
(52) U.S. Cl. ........................... 219/121.44; 219/121.57; 219/121.39; 219/121.48; 315/111.21
(58) Field of Search ....................... 219/121.57, 121.54, 219/121.39, 121.44, 121.36, 121.59, 121.48; 315/111.21; 313/231.31, 231.41; 606/48, 36–41; 607/97–102, 108, 109, 139, 105, 140, 152; 128/898

(56) References Cited

U.S. PATENT DOCUMENTS

| | | | |
|---|---|---|---|
| 3,663,858 A | 5/1972 | Lisitano | |
| 3,903,891 A | 9/1975 | Brayshaw | |
| 4,599,134 A | 7/1986 | Babu | |
| 4,691,090 A | 9/1987 | Garlanov | |
| 4,855,563 A | 8/1989 | Beresnev | |

(List continued on next page.)

OTHER PUBLICATIONS

Dull, Charles E., et al., *Modern Physics*, Henry Holt & Co., pp. 526–541, 1960.

(List continued on next page.)

*Primary Examiner*—Mark Paschall
(74) *Attorney, Agent, or Firm*—DLA Piper Rudnick; Gray Cary US LLP

(57) ABSTRACT

A device to place an incision into matter with a harmonious plasma cloud. A radiofrequency generator system produces pulsed or continuous electromagnetic waveform which is transmitted by an active transmitter incising electrode tip. This generated electromagnetic wave is utilized to initiate a plasma cloud with processes such as thermal ionization and a photoelectric effect which then trigger an Avalanche Effect for charged atomic particles at the surface of the active transmitter incising electrode tip. This electromagnetic wave is impedance matched, frequency matched, power matched and tuned to the plasma cloud in order to sustain and control a harmonious plasma cloud with reduced atomic particle turbulence and chaos. This harmonious plasma cloud forms a coating over the surface of the active transmitter electrode tip as well as acts to reduce the energy needed from the power amplifier of our plasma cutting device. The electromagnetic wave is also used to produce a Pinch Effect to compress, contour, shape and control the harmonious plasma cloud. The electromagnetic wave is furthermore used to trap and contain the plasma cloud without the need of a solid matter containment vessel according to the Magnetic Bottle Effect of physics and a generated centripetal electric field force that acts to pull plasma particles inward toward the activated incising electrode tip. The Tunnelling Effect of physical chemistry is utilized to focus and amplify the energy delivered to the harmonious plasma cloud while shielding matter surrounding the intended path of incision from potential electromagnetic radiation exposure. The invention is an efficient, effective, safe, clean and inexpensive device which can be used to place an incision in matter.

4 Claims, 2 Drawing Sheets

U.S. PATENT DOCUMENTS

| | | |
|---|---|---|
| 5,108,391 A | 4/1992 | Flachenecker |
| 5,217,457 A | 6/1993 | Delahuerga |
| 5,235,155 A | 8/1993 | Yamada |
| 5,300,068 A | 4/1994 | Rosar |
| 5,346,491 A | 9/1994 | Oertli |
| 5,558,671 A | 9/1996 | Yates |
| 5,591,301 A | 1/1997 | Grewal |
| 5,599,344 A | 2/1997 | Paterson |
| 5,628,745 A | 5/1997 | Bek |
| 5,647,869 A | 7/1997 | Goble |
| 5,669,907 A | 9/1997 | Platt |
| 5,669,975 A | 9/1997 | Ashtiani |
| 5,958,266 A | 9/1999 | Fugo et al. |
| 6,135,998 A | 10/2000 | Palanker |

OTHER PUBLICATIONS

Newman, James R., ed., *The Harper Encyclopedia of Science*, Harper and Row Publishers, pp. 923–924, 1967.

Newman, James R., ed. *The Harper Encyclopedia of Science*, Harper and Row Publishers, p. 697, 1967.

Milner, D.R. et al, *Introduction to Welding and Brazing*, Pergamon Press, pp. 64–83, 1968.

Friedman, Joshua, *The Technical Aspects of Electrosurgery*, J Oral Surgery, vol. 36, No. 2, pp. 177–187, 1973.

Besancon, Robert M. ed., *The Encyclopedia of Physics*, $2^{nd}$ ed., Van Nostrand Reinhold Co., pp. V–XIII; 851–853, 1974.

Sozio, Ralph B., et al. "A Histologic & Electronic Evaluation of Electrosurgical Currents: Non–Filtered full–wave modulated vs. Filtered Current," Journal of Prosthetic Dentistry, pp. 300–311, Mar. 1975.

Maness, W.L., et al., "Histologic Evaluation of Electrosurgery with Varying Frequency and Waveform," Journal of Prosethetic Dentistry, vol. 40, No. 3, pp. 304–308, 1978.

Krause–Hohnestein, U., *Electrosurgery: Fundamental Requirements for Use*, Quintessense International Nov. 1983, pp. 1115–1124.

Chen, Francis F. , *Introduction to Plasma Physics & Controlled Fusion*, Plenum Publishing Co., pp. I–XV, 1–17, 1983.

Ichimaru, Setsuo, *Statistical Plasma Physics, Vol. 1: Basic Principles*, Addison Wesley Publishing Co., pp. I–XIX, 1–28, 1992.

Ferris, Daron G., et al., "Gynecologic & Dermatologic Electrosurgical Units: A Comparative Review," Journal of Family Practice, vol. 39, No., 2, pp. 160–169, 1994.

The Lincoln Electric Co., "The Procedure Handbook of Arc Welding $13^{th}$ ed.," pp. 1.3–1 to 1.3–4, 1994.

Atkins, Peter, "Physical Chemistry, $5^{th}$ ed.", W.H. Freeman & Co., pp. 400–402, 1994.

Nishikawa, K., "Plasma Physics: Basic Theory with Fusion Applications," Spring–Verlay, pp. V–XIII, 1–55, 1994.

Goldston, Robert J., et al., *Intro to Plasma Physics*, Institute of Physics Publishing, pp. 132–135, 1995.

Ellman Surgitron FFPF & Surgitron Operating Manual ,pp,. 1–10 (no date).

Kemp, W., *NMR in Chemistry: A Multinuclear Introduction*, Macmillan Publishing Co., pp. 1–28, 1988.

Oler, R.C., "The 160 meter Band: An enigma shrouded in mystery—Part I," Amateur Radio CQ, vol. 54, No. 3, pp. 9–14, Mar. 1998.

Staar Surgical Symposium, "Plate Haptic Lens Implantation Techniques . . . The Bridge to the Future," R.J. Fugo, MD, PhD, The Plasma Blade, San Francisco, CA, Oct. 25, 1997.

ASCO Lecture Symposium, R.J. Fugo, MD, PhD, "The Plasma Blade," San Francisco, CA, Oct. 26, 1997.

Fugo, R.J., et al., "Devices Hone Electromagnetic Field Surgery: Plasma Blade Incises Tissue: Smart Blade Guides Path," Opthalmology Times, vol. 23, No. 3, pp. 4–5, Jan. 25, 1998.

ACES Lecture Symposium, Quality Surgery 12, R.J. Fugo, MD, PhD. "Electromagnetic Phacoemulsification," Lake Buena Vista, FL, Feb. 13, 1998.

Eyeworld editorial, "In Praise of the Pioneering Spirit," p. 5, "The Never Ending Quest: Creating a Better Way to Remove the Lens," pp. 50–51; "The Leading Edge: Harnessing Electrons For a Faster, Smarter Incision," p. 88, vol. 3, No. 4, Apr. 1988.

DEVICE FOR PLASMA INCISION OF MATTER WITH A SPECIFICALLY TUNED RADIOFREQUENCY ELECTROMAGNETIC FIELD GENERATOR

RELATED APPLICATIONS

The present application is a continuation of U.S. patent application Ser. No. 09/999,477, filed on Oct. 31, 2001, which is a continuation-in-part of U.S. patent application Ser. No. 09/112,471 filed on Jul. 9, 1998 now U.S. Pat. No. 6,479,785.

BACKGROUND

1. Field of Invention

This invention relates to a plasma generation device employed to place an incision into matter with a harmonious plasma cloud, specifically to harmonious plasma clouds initiated and sustained by electromagnetic energy waves transmitted from a radiofrequency signal generator system. This system is impedance matched, frequency matched and output power matched to the incising harmonious plasma cloud which is initiated, sustained and controlled by our device and in the process coats the activated transmitter incision probe of our invention.

2. Description of Prior Art

Hardened physical blades, such as a metal blade, a sapphire blade, or a diamond blade are the devices most frequently employed to place an incision into matter. Such incisions are based on frictional physical interactions between a sharp, acute edge of hardened matter against a surface of the matter to be incised. Such purely physical methods of one hardened matter attempting to cut through another hardened matter are inefficient and therefore experience significant inefficiencies such as frictional resistance when the matter being incised is solid and dense such as biologic tissue, wood products or even metal. For these reasons, others have resorted to devices such as electronically generated incisions, electro-incisions or electrosurgery of matter. When these types of devices are used to place an incision into matter, uncontrolled plasma arcs induce substantial burns or volatilization of matter while electrical ohmic resistance in the matter to be incised creates a heating effect due to phenomenon such as dielectric hysteresis and eddy currents. These last two phenomenon produce an effect known as diathermy which may result in a physical reaction that can produce an incision in matter. This approach has received limited use since its shortcomings include extensive damage to matter outside of the intended incision path with the resultant production of burning and charring which frequently causes unpleasant smelling fumes. The inefficiency of classic electro-incision units is manifested by the high power needed to produce a cutting effect at the incising tip, usually in excess of 50 watts of power. This relatively high power output needed in classic electro-cutting or electrosurgical units is secondary to the cutting inefficiency of these units which operate on a combination of classic ohmic diathermy as well as unstable, uncontrolled, caustic plasma arcing which is a form of disharmonious plasma.

Lasers have also been used to incise and cut; however, these units are expensive and require a large amount of system input energy to create a laser beam with sufficient power to cut or make an incision into matter. Lasers have been used to generate plasma and are used in processes such as etching in the field of microelectronics.

Plasma arcing can be found in a number of areas such as welding arcs, spark plug arcs, lightening bolt arcs, neon lights, fluorescent lights, and electrosurgical arcs. Uncontrolled arcing, per se, is a form of disharmonious plasma flow and represents uncontrolled flow turbulence of ionized atomic particles in plasma with a substantial level of atomic particles chaos in the plasma. The atomic particle turbulence in plasma arcs represents a form of atomic particle chaos and the uncontrolled nature of the atomic particle chaos causes a substantial quantity of energy spillover into matter outside of the intended path of incision and thereby may produce excessive heating. This level of substantial heating is produced when unwanted arcing occurs with classic electrocutting or electrosurgical units. This energy spillover into matter surrounding the intended path of incision into matter results in energy exposure and damage to the surrounding matter. Merely reducing the cutting tip power does not by itself significantly reduce the level of the plasma atomic particle chaos in as much as it does not greatly decrease the flow turbulence of the ionized atomic particles that comprise a plasma arc. Moreover, our invention uses an array of physical chemistry principles to minimize the atomic particle chaos of classic disharmonious plasma arcing as well as control the physical characteristics of the plasma produced by our device. Our invention minimizes disharmonious plasma arcing by reducing the atomic particle turbulence in the plasma cloud thereby greatly reducing the plasma cloud atomic particle chaos and thereby creating a harmonious plasma cloud. Harmonious plasma cuts in a more controlled, efficient and safer manner because the atomic particle components in a harmonious plasma cloud exist in a more stable, balanced, and controlled state with a higher order of organization and less atomic particle turbulence than disharmonious plasma. Our harmonious plasma cloud is furthermore compressed, controlled, contoured and shaped by utilizing the Pinch Effect of physics. Our compressed plasma cloud is then trapped and contained by the Magnetic Bottle Phenomenon and a centripetal electric field force that acts to pull plasma particles inward toward the activated transmitter incising tip; both principles well known to physicists and employed in fields such as nuclear physics. As opposed to classic electrocutting or electrosurgical units, our device cuts with a harmonious controlled plasma cloud rather than classic ohmic diathermy.

Accordingly, several objects and advantages of the present invention are:

(a) to provide an incisional device that uses an inexpensive electronic radiofrequency signal generator, amplifier, impedance matching and output conditioning network, as well as a transmitter probe to generate, amplify, condition and transmit an electromagnetic wave.

(b) to employ a solid, non-hollow conductive radiofrequency transmitter probe to create, maintain and control plasma. Nonetheless, the transmitter probe may be completely hollow or partially hollow in design.

(c) to produce a plasma cutting blade from an electronic electromagnetic field generator system which requires lower system input energy relative to other electrocutting incisional methods presently in use, even as low as 2 watts of average input power. Likewise, this system requires lower system output energy relative to other electrocutting incisional methods presently in use, even as low as 1 watt of average output power.

(d) to create a cutting plasma cloud without the necessity of injecting an ionizable gas into the field of cutting as is seen in plasma generating devices such as plasma torches and etching systems in plasma chambers.

(e) to create a harmonious plasma cloud with substantially reduced atomic particle chaos and turbulence than other plasma cutting devices by impedance matching and conditioning the energy from our electromagnetic generator system to the plasma cloud that surrounds and coats the activated transmitter incising electrode tip.

(f) to create a harmonious plasma cloud with substantially reduced atomic particle chaos and turbulence than other plasma cutting devices by frequency matching the energy from our electromagnetic generator system to the atomic particle oscillation harmonics and precession frequencies of the plasma cloud which coats and surrounds the activated transmitter incising electrode tip.

(g) to create a harmonious plasma cloud with substantially reduced atomic particle chaos and turbulence than other plasma cutting devices by power matching our electromagnetic generator system output power to the power requirements needed to initiate and sustain a harmonious plasma cloud.

(h) to produce a tightly coupled, high efficiency transfer of the electromagnetic waveform generator energy into the plasma cloud surrounding and coating the activated transmitter incising electrode tip thereby reducing the radiofrequency generator/amplifier output power needed to initiate and sustain a harmonious plasma cloud surrounding the activated transmitter incising electrode tip.

(i) to utilize the physics principle known as the Pinch Effect in order to concentrate, compress and contour the harmonious plasma cloud coating the activated transmitter incising electrode tip.

(j) to employ the physics principle known as the Magnetic Bottle Effect, as well as a centripetal electric field force acting to pull plasma particles inward toward the activated transmitter tip, thereby acting to trap and contain the harmonious plasma cloud and thereby eliminate the need of a solid matter confinement container to encase the plasma cloud. We thereby eliminate the need for a hollow plasma retention chamber near the activated transmitter incising electrode tip.

(k) to utilize the physical chemistry principle of Tunnelling to reflect the electromagnetic wave transmitted by the activated transmitter incising electrode tip off of matter surrounding the harmonious plasma cloud and thereby reflect the electromagnetic wave back into the harmonious plasma cloud surrounding the activated transmitter incising electrode tip. In this manner, we are employing the Tunnelling Effect to create an electromagnetic shield which minimizes transmitted electromagnetic radiation from interacting and penetrating into matter outside of the intended path of incision. This system acts to minimize the potential side effects of electromagnetic radiation exposure. Furthermore, this electromagnetic radiation reflected back into the plasma cloud acts to further energize the harmonious plasma cloud thereby further reducing the output energy required from the electromagnetic generator system to sustain the plasma cloud for effective cutting.

(l) to use a harmonious plasma cloud condensed around the activated transmitter incising electrode tip to focus the kinetic energy of the cutting plasma into a thinner cutting path in order to produce a discrete, clean incision into matter with minimal impact or side effects to matter outside of the intended path of incision.

(m) to produce an alternative to purely physical energy cutting techniques such as knives and metal blades, while also providing a more efficient, more effective, more precise, and cleaner cutting device than other cutting modalities presently available.

(n) to produce a less expensive cutting device than other high technology cutting devices commercially available, such as laser.

SUMMARY OF THE INVENTION

Our device is a specifically tuned radiofrequency generator and power amplifier system. Our invention does not require substantially complicated designs for the transmitter incising electrode tips nor elaborate plasma control devices such as a tokamak or cyclotron. The electromagnetic wave created by our system is a form of radiant electromagnetic energy and is transmitted from the active transmitter incising electrode tip of our system. This radiant electromagnetic energy is specifically conditioned to interact with atoms and molecules at the interface of the active transmitter incising electrode tip and the matter into which an incision is placed. The reaction of radiant electromagnetic energy with atoms and molecules at the incising electrode tip surface includes a photoelectric effect and thermal ionization which strip electrons from the atomic orbitals of atoms at the interface of the active incising electrode tip and the matter into which an incision is placed. The radiant energy acts to excite electrons and ions along the surface of the active transmitter incising electrode tip. The result of such processes is atomic transformation to higher energy ions and electrons. The free charged atomic particles move rapidly through space before colliding with electrons of other atoms in the electrode interface thereby knocking additional electrons out of their atomic orbitals. Repeating this process produces a chain reaction of charged atomic particle collision known as an Avalanche Effect which helps trigger the formation of a cloud of plasma along the active transmitter incising electrode tip surface. Our device is impedance matched, frequency matched, power matched and tuned to the plasma cloud coating the active transmitter incising electrode tip. Our device conditions the generated electromagnetic waveform to allow a tightly coupled, highly efficient energy transfer to the plasma cloud in order to provide maximum energy transfer into the plasma cloud with minimal loss of radiant electromagnetic energy into the matter surrounding the intended path of incision. Physical chemistry principles are employed to control the shape and characteristics of the plasma cloud, including the reduction of atomic particle chaos in the plasma cloud. In this way, our device produces a harmonious, controlled plasma that focuses energy into the intended path of incision as opposed to the caustic, disharmonious plasma arcing seen in classic electrocutting or electrosurgical units. This cloud of harmonious plasma manifests lower atomic particle chaos and produces a more efficient incision in matter than classic electrocutting or electrosurgical systems.

DETAILED DESCRIPTION OF THE PREFERRED EMBODIMENTS

Figure 1:
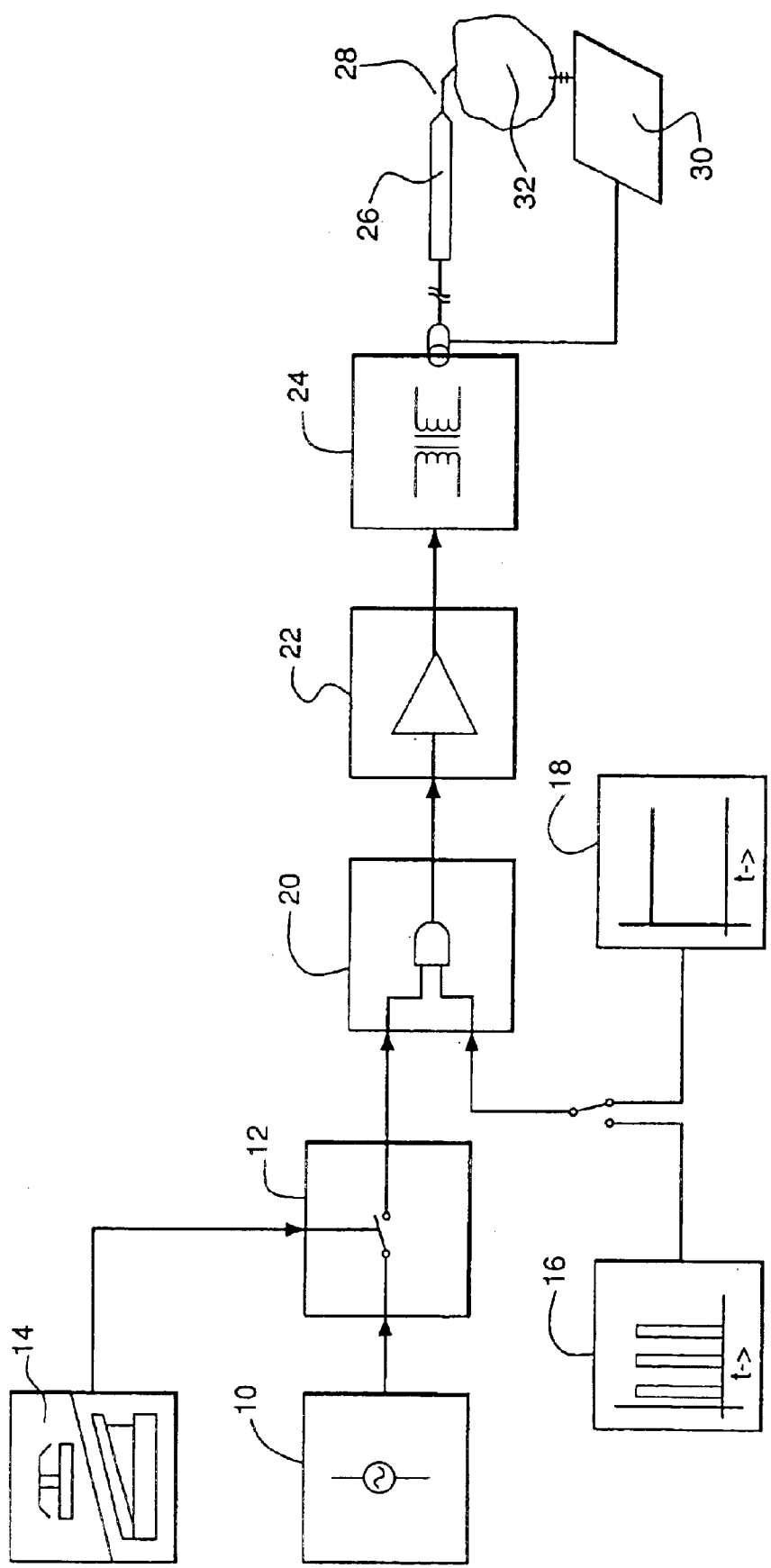
FIG. 1 shows a plasma cutting device with a capacitive coupling between the incising transmitter probe system and the matter into which an incision is placed.
Figure 2:
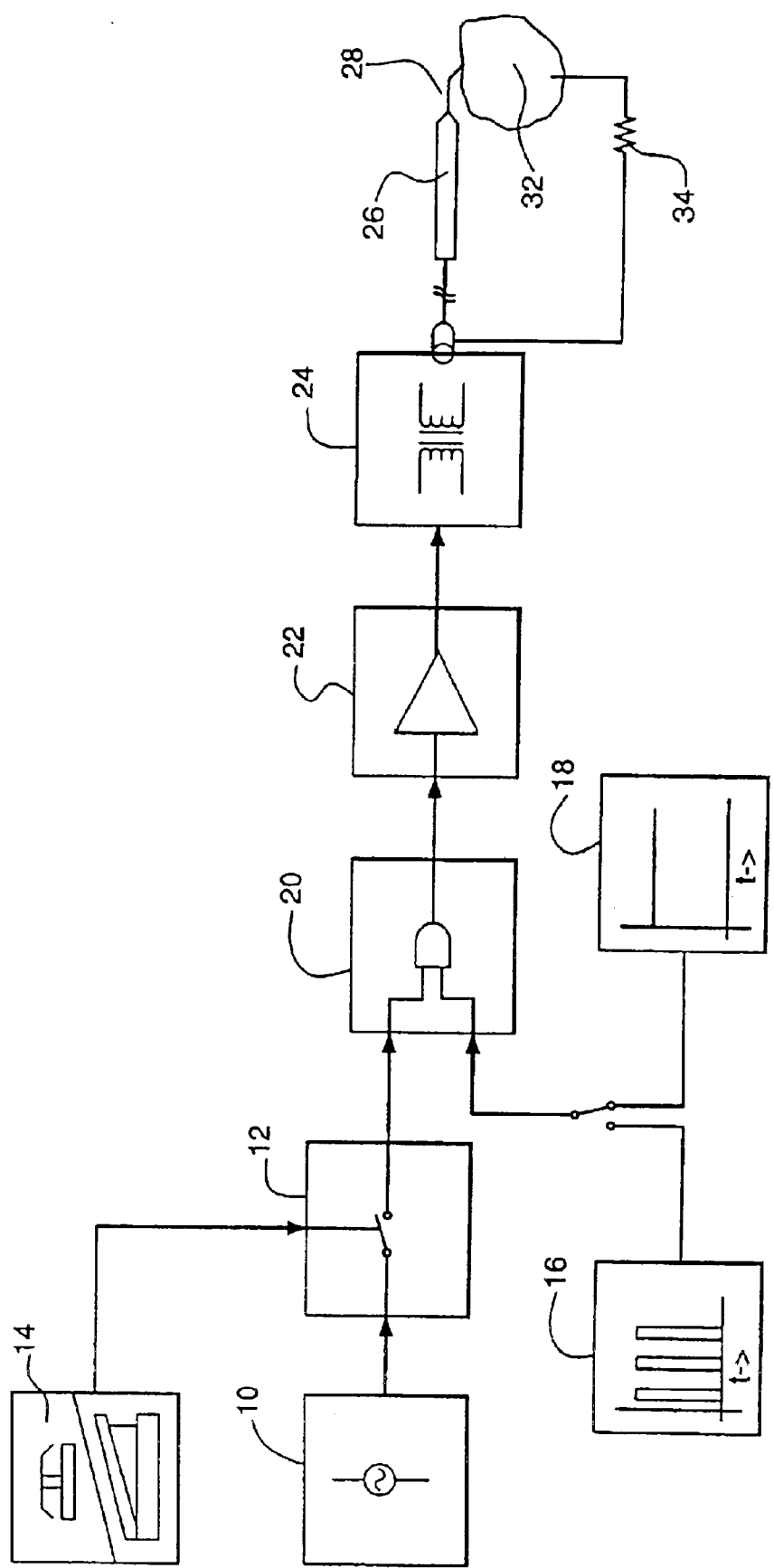
FIG. 2 shows a plasma cutting device with, a resistive coupling between the incising transmitter probe system and the matter into which an incision is placed.

A typical embodiment of the plasma incision device of the present invention is illustrated in FIG. 1 and FIG. 2. An output signal of a radiofrequency signal generator (10) is switched on and off with a radiofrequency switch (12) by several means such as an on-off button or on-off switch (14). The output signal of the radiofrequency signal generator is then slaved through a single gate (20) to either burst mode duty cycle generator (16) or a continuous mode free running generator (18). The burst mode or continuous mode radiofrequency output signal is then amplified through a power amplifier (22). The output signal of the power amplifier is then conditioned with an impedance matching and output conditioning network (24) and is then channeled into an active incising transmitter handpiece (26). When activated, an incising electrode tip (28) at the extreme end of incising transmitter handpiece (26) is coated with a plasma cloud which is used to place an incision path into the matter into which an incision is placed (32). Matter into which an incision is placed (32) may be coupled to our plasma cutting system either by a capacitive coupling plate (30) or a resistive coupling electrode (34). Active incising electrode tip (28) is preferably a solid, non-hollow conductor although a partial or completely hollow incising electrode tip may be utilized. Incising electrode tip (28) is preferably linear or curvilinear in design; however, the shape of incising electrode tip (28) is not necessarily specific in design and may even have a loop or polygon design.

Our invention for incising matter is different from all prior devices for incising matter. An on-off button/on-off switch (14) is used to activate or deactivate a radiofrequency switch (12). This therefore regulates the transmission of an output signal of a radiofrequency signal generator (10). Output signal of a radiofrequency signal generator (10) is further controlled such that its transmission is activated or deactivated by a burst mode duty cycle generator (16) or by a continuous mode free running generator (18). Output signal is amplified by a power amplifier (22) and then conditioned by an impedance matching and output conditioning network (24). Output signal is then channeled through an incising transmitter handpiece (26). Matter into which an incision is placed (32) may be linked to our invention by a capacitive coupling plate (30) or a resistive coupling electrode (34). Output signal is transmitted from a plasma cutting device by an incising electrode tip (28), creating a cloud of plasma to coat incising electrode tip (28). This plasma coat can react with atoms and molecules of matter and thereby place an incision path into matter into which an incision is placed (32).

Our system has similarities to standard radio transmission systems which are impedance matched to atmospheric air, whereas our system is impedance matched, frequency matched, power matched as well as tuned to a harmonious plasma cloud surrounding the active incising electrode tip (28). Although our invention bears similarities to other electromagnetic wave transmission systems, it employs and integrates a substantial number of principles of physics and chemistry in a manner which allows us to create a novel device to place a clean and efficient incision into matter.

The production of harmonious plasma around the active incising electrode tip (28) of our device results in a visible, organized plasma cloud which may be initiated, sustained and modified by our plasma cutting system. This harmonious plasma coating the activated incising electrode tip (28) also manifests substantially reduced atomic particle chaos and turbulence in the plasma cloud compared to other plasma cutting systems, thereby our device produces distinct visible and electronic characteristics.

The harmonious nature of this plasma cloud allows an increased concentration of energy in the intended path of incision with less energy spillover outside of the intended path of incision. Thereby, this device is able to achieve a cleaner, more precise, more powerful and more efficient incision with less impact on matter outside of the intended path of incision than classic electrocutting systems.

Plasma is the least abundant of the four types of matter to be found on earth, although it is the most abundant form of matter in the universe. Examples of plasma on earth include: welding arcs, spark plug arcs, neon light arcing, arcs around lightning discharges as well as uncontrolled, caustic plasma arcs seen in electrocutting or electrosurgery. Plasma is also used in fields such as semiconductor etching but is herein produced by expensive and high energy consumption systems such as lasers or elaborate plasma etching chambers. The levels of atomic particle turbulence and chaos manifested by classic electrocutting or electrosurgical units are employed by us as a relative standard for defining an increase or decrease in atomic particle turbulence or chaos in plasma.

Our system employs an inexpensive, electronic radiofrequency generator/amplifier system to produce, condition and transmit a continuous or pulsed electromagnetic field from an incising electrode tip (28). The cycle time of the electromagnetic field pulsed mode is variable and each complete on-off cycle of the pulsed mode may be as short as 0.000001 of a second. Specific parameters of this electromagnetic field generator system are largely determined by the atomic particle composition along the interface of the incising electrode tip (28) and the matter into which an incision is placed (32). Our system utilizes the atoms along the interface of the incising electrode tip (28) and the matter into which an incision is placed (32) to generate a plasma cloud as opposed to systems which require an ionizable gas to be injected into the field of incision and thereupon have the injected gas energized and converted into plasma. Nonetheless, our plasma cutting system may employ supplementary ionizable gas fed into the field of the incising electrode tip (28) in order to augment the cutting process. Our invention does not, however, require substantially complicated designs for the transmitter incising electrode tips nor elaborate plasma control devices such as a tokamak or cyclotron.

The electromagnetic wave created by our system is a form of radiant electromagnetic energy and is transmitted from the active incising electrode tip (28) of our system. The radiant electromagnetic energy is specifically conditioned to interact with atoms and molecules at the surface of the active incising electrode tip (28). Electromagnetic frequencies secondarily produced from atomic particle interaction and dynamics at the plasma incising electrode tip (28) play a substantial role in the system function and effectiveness. Harmonic frequencies of the fundamental generated electromagnetic waveform often play a substantial role in system function, dynamics and effectiveness. The radiant electromagnetic energy interaction with atoms and molecules includes thermal ionization and the photoelectric effect which strip electrons from the atomic orbitals of atoms at the interface of the matter into which an incision is placed (32) and the incising electrode tip (28). Such processes result in atomic transformation of atoms and molecules into ions and free electrons. The free charged atomic particles move through space before colliding with electrons of other electrode interface atoms thereby knocking more electrons out of their atomic orbitals. Repeating this process produces a chain reaction of charged atomic particle collision known as an Avalanche Effect which thereby participates in the formation of a cloud of plasma at the surface of the active incising electrode tip (28).

Our device is impedance matched, frequency matched, power matched and tuned to the plasma cloud coating the incising electrode tip (28). Our device conditions the transmitted electromagnetic waveform to provide a tightly coupled, highly efficient energy transfer to the plasma cloud in order to allow maximum energy transfer from the incising electrode tip (28) into the plasma cloud with minimal loss of electromagnetic radiant energy into the matter surrounding the intended path of incision. Physical chemistry principles are employed to control the shape and characteristics of the plasma cloud including the regulation of atomic particle chaos in the plasma cloud. In this way, our device produces a harmonious, controlled plasma that focuses energy into the intended path of incision as opposed to the caustic, disharmonious plasma arcing seen in classic electrocutting or electrosurgical units. This cloud of harmonious plasma possesses lower atomic particle chaos and turbulence than classic electrocutting or electrosurgical systems, thereby producing a more efficient incision into matter than found in classic electrocutting or electrosurgical systems which are seen to generate disharmonious plasma arcs.

The use of electromagnetic fields to regulate the order of atomic particles proliferates the literature of electronics, physics, and chemistry. Examples of the use of electromagnetic fields to create increased atomic particle order occurs frequently with modem technology and even includes turbine electric generators which produce electricity for our communities. Likewise, Nuclear Magnetic Resonance (NMR) devices use magnetic fields to transform randomly oriented atomic particles (a higher level of atomic particle chaos or disorganization) into atomic particles oriented in the plane of the magnetic field (a lower level of atomic particle chaos or disorganization). As an analogous process, our device employs an electromagnetic wave which is impedance matched, frequency matched, power matched and tuned to initiate, sustain and condition a plasma cloud around the incising electrode tip (28) as well as reduce the atomic particle disorganization and chaos in the plasma cloud. In this way, the atomic particles in the plasma cloud coating the incising electrode tip (28) of our invention are conditioned such that they possess less atomic particle chaos and a higher order of organization than seen in plasma arcs of classic electrocutting systems thereby allowing our device to generate a harmonious plasma cloud.

The levels of atomic particle turbulence and chaos manifested in classic electrocutting or electrosurgical units are employed by us to create a relative standard or baseline from which we may define and demonstrate an increase or decrease in the magnitude of atomic particle turbulence or chaos in plasma.

The effects of electromagnetic wave frequency and electromagnetic wave power or field strength are interrelated and dynamic. Nuclear Magnetic Resonance teaches us that precessing atomic particles may absorb radiant electromagnetic energy when that atomic particle precession frequency and the frequency of the radiant electromagnetic energy are in resonance. In other words, Nuclear Magnetic Resonance demonstrates that efficient absorption of electromagnetic energy occurs when the atomic particle is frequency matched to the radiant electromagnetic wave frequency. Our device demonstrates an analogous relationship regarding the importance of frequency matching our transmitter electromagnetic wave to the atomic particle properties composing the plasma cloud surrounding the incising electrode tip (28).

Nuclear Magnetic Resonance also teaches us that the frequency of atomic particle precession may be directly related to the strength of the magnetic field in which the atomic particle exists. Therefore, the stronger the applied magnetic field, the higher the electromagnetic field frequency required to achieve the resonance needed for efficient energy absorption. Likewise, the electron gyrofrequencies in the "D" and "E" layers of the earth's ionosphere substantially increase as we move from the equator toward the magnetic poles of the earth, either north pole or south pole. Respecting similar scientific principles, our device addresses the issue of field strength and electromagnetic frequency and thereby power matches and frequency matches our transmitted electromagnetic wave to the atomic particles composing the plasma cloud coating the incising electrode tip (28). Nonetheless, individual parameters of our electromagnetic field generator system vary substantially when placing an incision into different types of matter and are substantially dependent upon the atomic particle composition along the interface of the incising electrode tip (28) and the matter into which an incision is placed (32).

Strong interrelationships exist between a transmitted electromagnetic wave and the molecular composition surrounding the transmitter element. Ham radio operators utilize a measurement termed a Standing Wave Ratio to characterize the percentage of electromagnetic wave power transmitted into the atmosphere. The Ham radio unit may then have its transmitted electromagnetic waveform conditioned in order to maximize the percentage of electromagnetic energy transmitted into the atmosphere. Our device is analogous in that it maximizes transmitted electromagnetic radiation with an impedance matching and output conditioning network which provides a tightly coupled, highly efficient transfer of electromagnetic waveform energy into the plasma cloud which coats and surrounds the active incising electrode tip (28). In this manner, our device achieves an efficient transfer of radiant electromagnetic energy into the plasma cloud surrounding the incising electrode tip (28).

Arcing is a form of disharmonious plasma flow and represents uncontrolled, turbulent flow of ionized atomic particles in plasma, thereby producing increased atomic particle chaos and turbulence in the plasma. As has been shown in other fields such as Nuclear Magnetic Resonance (NMR), merely reducing the cutting tip power does not in itself significantly improve the plasma harmony in as much as it does not greatly decrease the flow turbulence or flow chaos of the ionized atomic particles that make up a plasma arc. As with other forms of matter, plasma has a wide range of physical presentation including a wide range of temperature, density, flow characteristics, atomic particle components, etc. On earth, plasma arcing can be found in a number of areas such as welding arcs, spark plug arcs, lightning bolt arcs, neon lights and electrocutting or electrosurgical arcs. The substantial intensity of atomic particle turbulence in classic electrocutting plasma arcs represents a form of elevated atomic particle chaos, wherein the uncontrolled nature of the atomic particle chaos is caused by turbulent flow of the atomic particles in the plasma cloud. This form of plasma represents disharmonious plasma and when used for cutting results in substantial heating or a significant quantity of energy spillover into matter outside of the intended path of incision. This energy spillover extending beyond the intended path of incision into matter results in energy exposure, thermal exposure and damage to surrounding matter. In this way, our invention minimizes classic plasma arcing by substantially reducing the atomic particle turbulence and chaos in the plasma cloud, and thereby acts to generate a harmonious plasma cloud.

As the electromagnetic field traverses the thin coating of harmonious plasma surrounding the activated incising electrode tip (28), the electromagnetic field is slowly damped or decreased in amplitude. Finally, the electromagnetic field will pass completely through the plasma cloud and will encounter matter outside of the intended incision path, namely the matter which surrounds the cloud of incising plasma. According to the physical chemistry principle of Tunnelling, the generated electromagnetic wave then encounters a barrier to which it is not tuned nor impedance matched and thereby a substantial percentage of the remaining energy of the electromagnetic wave is reflected back into the harmonious plasma cloud. This reflected electromagnetic energy acts to further energize the molecular particles in the plasma cloud, thereby reducing the output energy which must be transmitted by the electromagnetic wave generator system. This process also serves to minimize the percentage of total electromagnetic radiation that penetrates into, that reacts with, and that presents potential radiation exposure damage to matter outside of the intended incision path.

The centripetal force of our generated electromagnetic field is used to control the distance between the atomic particles in the harmonious plasma cloud and the surface of the activated incising electrode tip (28). The ionized particles travel in spiral paths in magnetic fields while the individual ionized particles may simultaneously be oscillating, vibrating, spinning and/or precessing. Furthermore, the Pinch Effect which has been used for many years in fields such as plasma physics is employed in our system. In this way, we are able to compress, contour, shape and control the harmonious plasma cloud with a solid or hollow transmitter incising electrode tip (28). We also employ the Magnetic Bottle Effect used in fields such as nuclear physics, as well as a centripetal electric field force, to trap and contain the compressed plasma cloud without the need of solid matter containment vessels and thereby avoid the requirement to employ hollow or cavity containing incising tip probes to trap and control the plasma cloud. Increasing the density of atomic particles in the harmonious plasma cloud allows us to substantially increase the plasma cloud power density, thereby improving the cutting efficiency and power of the plasma cloud.

Furthermore, compressing the plasma cloud causes a substantial decrease in the cross sectional diameter of the plasma cloud thereby decreasing the width of the intended incision path as well as minimizing side effects or potential adverse impact on matter outside of the intended path of incision. Once the electromagnetic wave generator system has its power turned off, the energy level of the harmonious plasma cloud rapidly decays to a point at which the atomic particles comprising the plasma cloud cannot be sustained in the state of matter known as plasma.

Accordingly, the reader will see that employing a specifically tuned electromagnetic wave to generate a harmonious plasma which may have its shape, contour, power density and physical characteristics controlled allows us to produce a more efficient, more controlled, less toxic and more cost effective method of incising matter.

Whereas classic electrocutting or electrosurgical units employ inefficient classic ohmic diathermy to produce incision into matter, our radiofrequency generator system utilizes its conditioned, transmitted power to create and sustain a thin cloud of harmonious plasma which coats the incising electrode tip. Thereby, less energy is required by our invention than classic ohmic electrocutting or electrosurgical systems. The incision into matter produced by our invention is created by the interaction of the harmonious plasma cloud coating our incising electrode tip and the matter into which an incision is placed. In effect, an incision into matter is created by the energy of a controlled, harmonious cloud of plasma atomic particles surrounding an activated incising electrode tip. Furthermore, our plasma incising device has the additional advantages in that it permits an inexpensive production of plasma;

it permits an efficient production of plasma;

it permits a controllable production of plasma;

it permits the production of a plasma which may place an incision into solid matter;

it employs known physical principles to maximize transfer of radiant electromagnetic energy into the generated plasma cloud;

it employs known scientific principles to allow radiant electromagnetic energy to interact with, stimulate, and energize atomic particles which themselves may be oscillating, vibrating, spinning, and/or precessing.

it provides the production of a plasma with lower atomic particle chaos and lower atomic particle turbulence than produced with classic plasma cutting devices, thereby allowing the production of a harmonious plasma;

it produces an incision into matter with a thinner corridor of matter involved in the path of incision;

it produces an incision into matter which utilizes the Tunnelling Effect of physical chemistry to shield matter outside of the intended path of incision from electromagnetic radiation, thereby eliminating the need to employ shields constructed of various forms of matter;

it utilizes a centripetal electric field force and a magnetic field force to trap the created plasma around the incising electrode tip;

it utilizes the Pinch Effect to compress, contour and control both the shape and density of the plasma cloud, thereby eliminating the need for bulky containment chambers to encase the generated plasma;

it eliminates the need for substantially complicated designs for transmitter incising electrode tips;

it eliminates the need for elaborate plasma control devices or chambers such as a tokamak or cyclotron; and it produces an incision into matter which is inexpensive, clean, efficient, safe and controllable.

Although the plasma incision device described above may be utilized to cut many different types of matter, the present inventors have discovered the following optimal operating parameters for cutting ocular tissue (particularly during a capsulotomy procedure):

| | |
|---|---|
| Output Voltage ($V_{p-p}$) | 180–230 Volts |
| Output Frequency (MHz) | 9.8–9.9 MHz |
| Pulsed Peak Output Power (Watts) | 9.0–14.7 Watts Peak RMS |
| Average Output Power (Watts) | 0.40–1.82 Watts |
| Duty Cycle | 4.48–12.37% (on time) |
| Total Burst Cycle Time (mS) | 20.5–24.5 milliseconds |
| Burst On-Time (mS) | .92–3.03 milliseconds |
| Output Impedance (Ohms) | 400–600 Ohms |

| -continued | |
|---|---|
| Burst Modulation | Square Wave |
| Carrier Modulation | Sine Wave |
| Transmitter Incising Electrode Tip Material | #304 Stainless Steel |
| Transmitter Incising Electrode Tip Shape | Solid tubular |
| Transmitter Incising Electrode Tip Dimensions | .75 mm in length; 100 microns in cross-section |

It will be noted by those skilled in the art that in order to properly incise other types of matter (i.e., matter other than ocular tissue), an empiric calculation must be performed to determine the above values for the particular type of matter. First, a standard caustic disharmonious plasma arc is usually required as an initial baseline plasma field. This initial plasma arc may require high power levels (e.g., 50–500 watts average power) because of inefficient power transfer from the electronics into the intended path of incision. Then, an empiric interdependent variation of frequency, impedance and system power will allow the scientist to achieve the correct variable combination which provides maximum efficiency of power transfer into the intended path of incision as well as the creation of a sustained harmonious plasma cloud. After one variable (e.g., frequency) is altered and an optimum level is discovered, then the second variable (e.g., output impedance) is altered, then the third variable (e.g., output power) is altered based on improved energy transfer and improved characteristics of the plasma cloud. The frequency, impedance and power parameters may be altered through the use of the radiofrequency generator 10, one of the duty cycle generators 16, 18, and the conditioning network 24. The above sequence must be repeated numerous times until the desired 'harmonious' plasma cloud is created.

The present invention involves empirically impedance matching, power matching and frequency matching an electronic system to an unrefined plasma cloud which is empirically improved and refined into a 'harmonious' plasma cloud. For example, too little system power will cause extinguishment of the plasma cloud, whereas too much system power will cause the plasma cloud to loose its 'harmonious' character and moreover become explosive and uncontrolled. As the appropriate system parameters are approached, the system power requirements will decrease while the integrity of the harmonious plasma cloud increases. The refined 'harmonious' plasma cloud may be observed electronically and visually (e.g. through a high resolution microscope).

Although the description above contains many specifications, these should not be construed as limiting the scope of the invention but as merely providing illustrations of some of the presently preferred embodiments of this invention. Thus, the scope of the invention should be determined by the appended claims and the legal equivalents, rather than the examples given.

We claim:

1. A device to produce an incision into matter using plasma comprising:

a radiofrequency source;

a probe having a first electrode for applying at least one radiofrequency pulse generated by the radiofrequency source to matter and a second electrode, said second electrode comprising a resistive electrode for providing a discrete resistance between the first electrode and the second electrode;

a switch coupled between the radiofrequency source and the first electrode so that the discharge switch applies said at least one radiofrequency pulse to the first electrode when the switch is closed.

2. The device of claim 1, further comprising:

at least one amplifier coupled between the radiofrequency source and the first electrode.

3. The device of claim 2, further comprising:

at least one logic gate coupled between the at least one amplifier and the switch.

4. The device of claim 2, further comprising:

at least one transformer coupled between the at least one amplifier and the first electrode.

* * * * *